United States Patent [19]

Dabora et al.

[11] Patent Number: 5,159,104
[45] Date of Patent: Oct. 27, 1992

[54] PROCESS TO SIMVASTATIN ESTER

[75] Inventors: Rebecca L. Dabora, Andover, Mass.; Gregory L. Tewalt, Shenandoah, Va.

[73] Assignee: Merck & Co., Inc., Rahway, N.J.

[21] Appl. No.: 694,164

[22] Filed: May 1, 1991

[51] Int. Cl.$^5$ ................... C07C 69/74; C07D 309/30
[52] U.S. Cl. ................................. 560/119; 549/292
[58] Field of Search ......................... 560/119; 549/292

[56] References Cited

U.S. PATENT DOCUMENTS

| | | | |
|---|---|---|---|
| 4,293,496 | 10/1981 | Willard | 549/292 |
| 4,444,784 | 4/1984 | Hoffman et al. | 549/292 |
| 4,582,915 | 4/1986 | Sleteinger et al. | 549/292 |
| 4,584,389 | 4/1986 | Sletzinger et al. | 549/292 |
| 4,820,850 | 4/1989 | Verhoeven et al. | 549/292 |
| 4,866,090 | 9/1989 | Hoffman et al. | 560/119 |

FOREIGN PATENT DOCUMENTS 0303952 12/1988 Japan .
2073193 3/1981 United Kingdom .

OTHER PUBLICATIONS

W. F. Hoffman et al., II. 3-Hydroxy-3-Methyl-glutaryl-Coenzyme A Reductase Inhibitors, *J. Med. Chem.,* 29, 849 (1986).

*Primary Examiner*—C. Warren Ivy
*Assistant Examiner*—A. A. Owens
*Attorney, Agent, or Firm*—Joseph F. DiPrima; Melvin Winokur; David A. Muthard

[57] ABSTRACT

A process is disclosed, for the formation of simvastatin, which comprises the sequential acylation of a diol lactone to form a bis acylated intermediate followed by selective deacylation and lactone ring closure to form simvastatin.

4 Claims, No Drawings

PROCESS TO SIMVASTATIN ESTER

BACKGROUND OF THE INVENTION

Hypercholesterolemia is known to be one of the prime risk factors for atherosclerosis and coronary heart disease, the leading cause of death and disability in western countries. The bile acid sequestrants seem to be moderately effective as antihyperchloesterolemic agents but they must be consumed in large quantities, i.e., several grams at a time, and they are not very palatable.

MEVACOR ® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof. For example, simvastatin, wherein the 8-acyl moiety is 2,2-dimethylbutyryl, is an even more potent HMG-CoA reductase inhibitor than lovastatin.

Simvastatin is now commercially available as ZOCOR ® in some markets.

The preparation of simvastatin was originally described in U.S. Pat. No. 4,444,784. The process involves deacylation of lovastatin followed by a subsequent acylation with the 2,2-dimethylbutyryl moiety. Simvastatin has also been prepared by the alpha alkylation of the lovastatin ester moiety as described in U.S. Pat. Nos. 4,582,915 and 4,820,850.

The recent commercial introduction of simvastatin has provided a need for a high yielding process for the production of simvastatin, which is economically efficient and environmentally sound.

DETAILED DESCRIPTION OF THE INVENTION

This invention relates to a process for the formation of simvastatin, which comprises the sequential acylation of a diol lactone (I) to form a bis acylated intermediate (III) followed by selective deacylation and lactone ring closure to form simvastatin (VI). The overall process is outlined in Scheme 1.

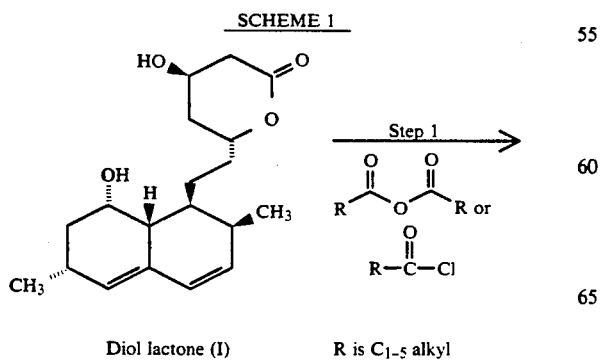

Diol lactone (I)    R is $C_{1-5}$ alkyl

-continued
SCHEME 1

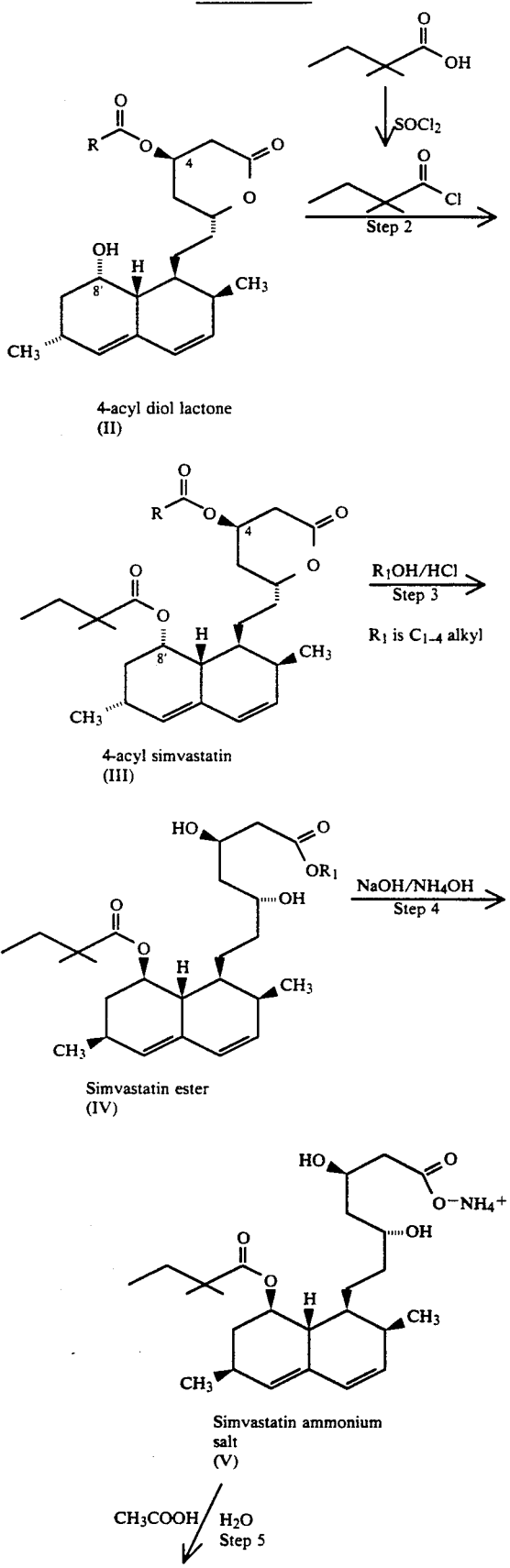

4-acyl diol lactone (II)

4-acyl simvastatin (III)

$R_1$ is $C_{1-4}$ alkyl

Simvastatin ester (IV)

Simvastatin ammonium salt (V)

-continued
SCHEME 1

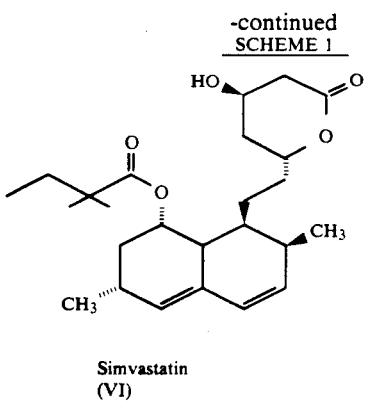

Simvastatin
(VI)

The diol lactone (I) may be prepared following the description in U.S. Pat. No. 4,293,496.

The diol lactone (I) is initially acylated at the lactone hydroxyl moiety employing an acid anhydride (R—CO)$_2$O or an acyl halide R—COCl, wherein R is C$_{1-5}$ alkyl, to form a 4-acyl diol lactone compound of formula (II). Compound (II) is then acylated at the 8'-position of the polyhydronaphthyl ring with 2,2-dimethylbutyryl chloride or 2,2-dimethylbutyryl bromide to form a 4-acyl simvastatin compound of formula (III).

The diacyl intermediate of formula (III) is deacylated at the 4-position of the lactone ring using an alcohol R$_1$OH, wherein R$_1$ is C$_{1-4}$ alkyl, and an acid to form the simvastatin ester compound (IV) which is then treated with ammonium hydroxide to form the ammonium salt (V). The acid may be selected from the group consisting of hydrochloric, sulfuric and acetic acid, however those skilled in the art will appreciate that other acids can be effective and are included within this invention. The lactone ring is closed and simvastatin (VI) formed by treating the ammonium salt (V) with a dilute acid such as acetic acid, or hydrochloric acid or sulfuric acid.

EXAMPLE 1

Preparation of
6(R)-[2-[8'(S)-(2'',2''-dimethylbutyryloxy)-2'(S),6'(R)-dimethyl-1',2',6',7',8',8a'(R)-hexahydronaphthyl-1'(S)]ethyl-4(R)-hydroxy-3,4,5,6-tetrahydro-2H-pyran-2-one (a) Preparation of
6(R)-[2-[8'(S)-hydroxy-2'(S),6'-(R),-dimethyl-1',2',6',7',8',8a'(R)-hexahydronaphthyl-1'(S)]ethyl-4(R)-acetyl-3,4,5,6-tetrahydro-2H-pyran-2-one (2)

To crude, dry diol lactone (I) (5.0 g; 0.0156 mol) and 4-dimethylamino pyridine (DMAP) (0.3813 g; 0.0031 mol; 20 mol %) in dry pyridine (30 mL) at 0° Celsius under nitrogen was added acetic anhydride (1.77 mL; 0.017 mol) in one shot and the mixture stirred for 4–6 hours at 0° Celsius.

The pyridine was evaporated and ethyl acetate was added (60 mL). The solution was washed with saturated NaCl (60 mL), the layers separated, and the organic layer dried over molecular sieves. The organic layer was filtered and the ethyl acetate was evaporated off to give a light brown solid.

Alternative to the above, the reaction mixture was worked up by addition of ethyl acetate (60 ml) followed by washing with saturated copper sulfate (4×50 ml), separating the the layers and drying the organic layer over anhydrous magnesium sulfate or anhydrous sodium sulfate. The organic layer was filtered and the ethyl acetate was evaporated off to give a light brown solid, identified as the title compound.

(b) Preparation of 2,2-Dimethylbutyryl chloride

To 2,2-dimethylbutyric acid (24.04 g; 0.207 mol) at room temperature under nitrogen was added thionyl chloride (16.6 mL; 0.227 mol) and the mixture stirred for 5 hours. The product was distilled (29 in. Hg) at 52°–53° C. to give a clear liquid.

(c) Preparation of
6(R)-[2-[8'(S)-(2'',2''-dimethylbutyloxy)-2'(S),6'(R)-dimethyl-1',2',6',7',8',8a'(R)-hexahydronaphthyl-1'(S)]ethyl-4(R)-acetyl-3,4,5,6-tetrahydro-2H-pyran-2-one (3)

The crude 4-acetylated diol lactone compound (2) (3.15 g; 0.0087 mol) under nitrogen was dissolved in dry pyridine (8.7 mL); DMAP (0.2126 g; 0.0017 mol; 20 mol %) was added and the temperature was decreased to 0° C. 2,2-dimethylbutyryl chloride (9.37 g; 0.0696 mol; 8 equivalents) was added over 10 minutes and the mixture was stirred for 0.5–1.0 hours at this temperature. The reaction temperature was then increased to between 35°–40° C. and stirred for 48 hours.

The pyridine was evaporated and ethyl acetate was added (20 ml). The solution was washed with saturated NaCl (20 ml), the layers separated, and the organic layer dried over molecular sieves. The organic layer was filtered and the ethyl acetate was evaporated to give a light brown solid.

Alternative to the above the reaction mixture was worked up by addition of ethyl acetate (60 ml) followed by washing with saturated copper sulfate (4×50 ml), separating the the layers and drying the organic layer over anhydrous magnesium sulfate or anhydrous sodium sulfate. The organic layer was filtered and the ethyl acetate was evaporated off to give a light brown solid, identified as the title compound.

(d) Preparation of Simvastatin Methyl Ester (4)

To 4-acetyl simvastatin (compound 3) (5.0 g; 0.11 mol) in dry methanol (100 mL) at room temperature under nitrogen was slowly added concentrated HCl (30 mL) while maintaing ambient temperature and the reaction stirred for 16 hours. The methanol was evaporated, ethyl acetate (100 mL) was added, and the mixture was washed with saturated sodium bicarbonate (2×50 mL) to neutralize the excess HCl. The layers were separated, and the organic layer dried over molecular sieves. The organic layer was filtered and the ethyl acetate evaporated off to give a light yellow oil, identified as the title compound.

(e) Preparation of Simvastatin Ammonium Salt (5)

Deionized water (127 mL) was added to simvastatin methyl ester (compound 4) (4.24 g; 0.0094 mol) at room temperature under nitrogen. Solid NaOH (3.76 g; 10 equivalents) was added while maintaining ambient temperature. The reaction was stirred for 1–2 hours and cooled to 0° Celsius. The pH was adjusted to 7.0 using 2N HCl and ethyl acetate (67 mL) was added. The pH was adjusted to 4.0 using 2N HCl and the two phases were stirred for 30 minutes. Methanol (2.5 mL) was added to the organic layer and the temperature adjusted to 10° Celsius. 1:3 ammonium hydroxide:methanol (5.3 mL) was added over 30 minutes; seeding with 50 mg of pure simvastatin ammonium salt may be necessary at this point to initiate crystallization. The mixture was aged for 2 hours at 0° C., the slurry was filtered and the cake was washed with cold 9:1 ethyl acetate:methanol (9.5 mL). The product was dried to give a light pink solid, identified as the title compound.

(f) Preparation of
6(R)-[2-[8'(S)-(2'',2''-dimethylbutyryloxy)-2'(S),6'(R)-dimethyl-1',2',6',7',8',8a'(R)-hexahydronaphthyl-1'(S)]ethyl-4(R)-hydroxy-3,4,5,6-tetrahydro-2H-pyran-2-one (6)

Deionized water (20 mL), glacial acetic acid (40 mL) and butylated hydroxyanisole (BHA, 50 mg) were charged to a 250 mL 3 neck round bottom flask under a nitrogen atmosphere. The batch temperature was adjusted to 20°-25° C. and simvastatin ammonium salt (compound 5) (12.5 g, assay basis, 27.56 mmoles) was added and agitated at 20°-25° C. for 15 minutes or until dissolved. Methanesulfonic acid (70%, d=1.35, 4.23 g, 30.8 mmoles, 1.118 equiv.) was added and the mixture aged at 20°-25° C. for 2 hours until the lactonization reaction had gone to >75% completion.

The mixture was seeded with simvastatin crude seed (60 mg) and aged at 20°-25° C. for 0.5 hours. Deionized water (22.5 mL) was added over 3 hours (0.13 mL/min.) and a second deionized water charge (35 mL) added over 1 hour (0.58 mL/min). The mixture was aged at 20°-25° C. for 1 hour then treated with 28 v/v % ammonium hydroxide (4.0 mL).

The mixture was aged at 20°-25° C. for 1 hour and filtered to collect the simvastatin crude crystals. The simvastatin crude wet cake was washed with (2:1) deionized water/acetic acid (50 mL), and deionized water (50 mL) and (1:1) methanol/deionized water (50 mL). The product was dried overnight in vacuo with a nitrogen purge at 25°-30° C. to give simvastatin crude as white needles (HPLC assay=98% by weight).

HPLC weight % assay for dry Simvastatin crude is performed under the following conditions:

Accurately weigh 30 mg of standard (or sample) into a 100 mL volumetric flask and dissolve in 60:40 acetonitrile: 0.01M $KH_2PO_4$ (pH=4.0) to 100 ml final volume.

The average response factor is determined by HPLC analysis under the following conditions:
Column: Perkin-Elmer $C_{18}$-3 cm length, 3 micron particle size
Temperature: 25° C.
Flow rate: 3.0 mL/min
Detection: UV 238 nm
Injection: 5 microliters
Mobile phase: 50:50 acetonitrile: 0.1% $H_3PO_4$ (aq.)

| Retention Time min. | Identity |
|---|---|
| 1.80 | 1. Simvastatin ammonium salt |
| 2.20 | 2. Lovastatin and epimer |
| 3.44 | 3. Simvastatin crude |

The weight % was calculated as follows:

$$\frac{(\text{average response factor of samples})(100)}{(\text{average response factor of Standard})} = \text{weight \%}$$

EXAMPLES 2-4

Simvastatin was prepared from intermediate (III) wherein R was n-propyl or isopropyl. Intermediate (II) in the sequence was prepared following Example 1 (a) but substituting an equivalent amount of butyric anhydride, isobutyric anhydride, or butyryl chloride or isobutyryl chloride for the acetic anhydride of Example 1 (a).

What is claimed is:

1. A process for the formation of a compound (IV) which comprises the treatment of a compound (III), wherein R is $C_{1-5}$ alkyl:

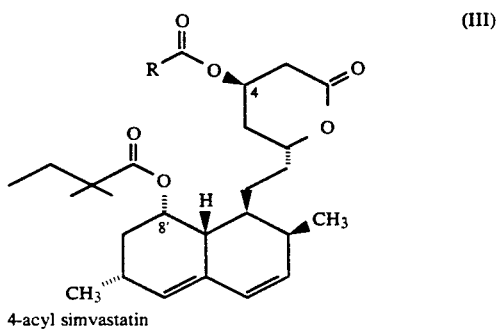

4-acyl simvastatin with an alcohol $R_1OH$, wherein $R_1$ is $C_{1-4}$ alkyl, and an acid to yield a compound of formula (IV):

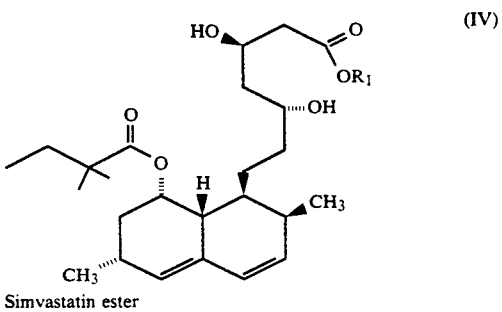

Simvastatin ester

2. A process of claim 1 wherein the acid is selected from the group consisting of: hydrochloric, sulfuric, and acetic.

3. A process of claim 2 wherein the alcohol is selected from methanol, ethanol, n-propanol, isopropanol and t-butanol and the acid is hydrochloric acid.

4. A process further comprising the treatment of a diol lactone (I)

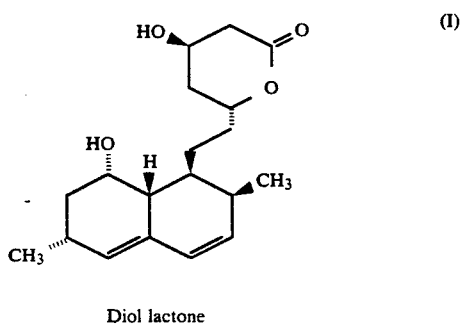

Diol lactone with an acylating agent selected from $(RCO)_2O$ or $RCOCl$, wherein R is $C_{1-5}$ alkyl, to yield a compound (II):

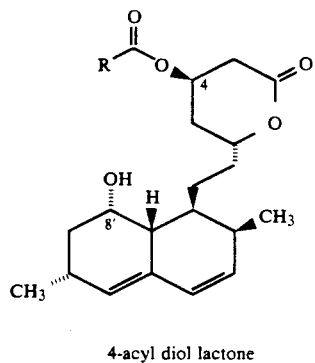
4-acyl diol lactone (II)
followed by treatment of compound (II) with 2,2-dimethylbutyryl chloride to yield a compound (III).
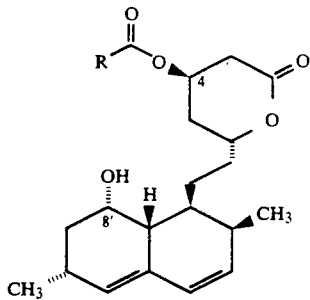
4-acyl diol lactone (II)
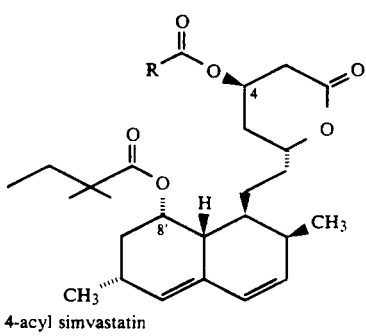
4-acyl simvastatin (III)
* * * * *